United States Patent [19]
Kato et al.

[11] Patent Number: 5,925,183
[45] Date of Patent: Jul. 20, 1999

[54] METHOD FOR PRODUCING LAYER-STRUCTURED PEROVSKITE THIN FILM OF BISMUTH-BASED COMPOUNDS HAVING FERROELECTRIC PROPERTIES

[75] Inventors: Kazumi Kato, Aichi, Japan; Sandwip Kumar Dey, Tempe, Ariz.

[73] Assignee: Japan as represented by Director General of Agency of Industrial Science and Technology, Tokyo, Japan

[21] Appl. No.: 09/022,005

[22] Filed: Feb. 11, 1998

[30] Foreign Application Priority Data

Sep. 1, 1997 [JP] Japan ................................. 9-252926

[51] Int. Cl.$^6$ .............................. C09D 4/00; C07F 9/94; C07F 17/00; C07F 19/00
[52] U.S. Cl. ......................................... 106/287.18
[58] Field of Search ......................... 106/287.18

[56] References Cited

U.S. PATENT DOCUMENTS 5,516,363  5/1996  Azuma et al. .................. 106/287.18
5,788,757  8/1998  Uchida et al. ................... 106/287.18

OTHER PUBLICATIONS

De Araujo, et al., "Fatigue–free Ferroelectric Capacitors with Platinum Electrodes," Nature, vol. 374, (Apr. 13, 1995,) pp. 627–629.

Boyle, et al., "Formation of $SrBi_2Ta_2O_9$: Part I. Synthesis and Charaterization of a Novel "Sol–Gel"Solution for Production of Ferroelectric $SrBi_2Ta_2O_9$ Thin Films," J. Mater. Res., vol. 11, No. 9, (Sep. 1996,) pp. 2274–2281.

Ravichandran, et al., "Alkoxide Derived $SrBi_2Ta_2O_9$ Phase Pure Powder and Thin Films,"Journal of Sol–Gel Sciences and Technology 9, (1997), No Month Avail. pp. 95–101.

*Primary Examiner*—David Brunsman
*Attorney, Agent, or Firm*—Oblon, Spivak, McClelland, Maier & Neustadt, P.C.

[57] ABSTRACT

The present invention relates to a method for producing an Sr—Bi—Ta or Nb-based composite alkoxide with the structure of an atomic arrangement controlled, having a metal atomic ratio of Sr:Bi:Ta or Nb=1:2:2, characterized in that an Sr alkoxide ($Sr(OR)_2$) prepared from an Sr metal is allowed to react with a Bi alkoxide ($Bi(OR)_3$) in alcohol to produce an Sr—Bi double alkoxide ($Sr[Bi(OR)_4]_2$), and subsequently the alkoxide is allowed to react with a Ta alkoxide ($Ta(OR)_5$) or an Nb alkoxide ($Nb(OR)_5$).

3 Claims, 6 Drawing Sheets

METHOD FOR PRODUCING LAYER-STRUCTURED PEROVSKITE THIN FILM OF BISMUTH-BASED COMPOUNDS HAVING FERROELECTRIC PROPERTIES

DESCRIPTION OF THE INVENTION

The present invention relates to a method of preparation of a precursor composite alkoxide for a layer-structured perovskite ferroelectric thin film of bismuth-based compounds, the synthesis of a layer-structured perovskite ferroelectric thin film of bismuth-based compounds, and techniques of utilization thereof; in particular, the present invention relates to a method of the production of a precursor composite alkoxide suitable for low-temperature crystallization which realizes the low temperature processes, the low-temperature crystallization of a thin film employing said composite alkoxide, and techniques of utilization applying the ferroelectric properties thereof.

BACKGROUND OF THE INVENTION

Thin films of layer-structured perovskite compounds such as $SrBi_2Ta_2O_9$(SBT), $SrBi_2Nb_2O_9$(SBN) and their solid-solutions ($SrBi_2(Nb_xTa_{1-x})_2O_9$, SBNT) are promising materials for nonvolatile ferroelectric memory applications because of their excellent ferroelectric properties, especially with respect to fatigue performance.[1] The solid solutions, $SrBi_2M_2O_9$ (M; Ta, Nb), known as Aurivillius compounds consist of a stack of alternating layers of $(Bi_2O_2)^{2+}$ with two pseudo-perovskite layers of oxygen octahedra, $(SrM_2O_7)^{2-}$ (M; Ta, Nb) in the c-direction. The high spontaneous polarization is parallel to the plane of the layers (in the a- and b-directions), as this plane contains the O—M—O (M; Ta, Nb) chains that are known to have high polarizibilities as in the perovskite ferroelectrics. It has been suggested that weak fatigue is due to weak pinning of domain boundaries by trapped carriers at shallow Bi and M (M; Ta, Nb) centers.[2]

For these systems, it is imperative that the processing temperatures be lowered below 800° C., since reactions at the bottom electrode-thin film interface cause degradation of electrical properties.[1)–5)]

Usually, nonstoichiometric Bi-excess compositions have been used to compensate for the loss of Bi to the substrate during heat treatments. A recent report suggests that fatigue performance is a function of the composition, and nonstoichiometric thin films exhibited low fatigue compared to stoichiometric thin films.[3)] Thus, if the molecular structure and the stoichiometry of the precursors can be controlled, a stack of alternating layers of $(Bi_2O_2)^{2+}$ with two pseudo-perovskite layers of oxygen octahedra $(SrM_2O_7)^{2-}$ (M; Ta, Nb) in the Aurivillius compounds may be formed at lower temperatures, thereby improving the ferroelectric properties.

To date, there are many reports on the sol-gel method in a broad sense, [3]–[8] but only one report discusses the solubility and coordination of bismuth acetate in a solvent. [6] The precursor structure, however, for the layer-structured perovskite thin films has not been reported.

In addition, it has been investigated to make a film thin by the laser abrasion method, the MOCVD method, the sol-gel method and the like; however, they have a problem in common that the processes require a high temperature.

The present inventors studied the molecular structure of the oligomeric precursors for the layer-structured perovskite thin films and the development of the inorganic oxide structure from the precursors, particularly, low-temperature crystallization and the cause thereof. We described the suitable precursor chemistry and the molecular structure of the oligomeric precursors for the layer-structured perovskite thin films elsewhere.[4)–10)] In this invention, the development of the inorganic oxide structure from the alkoxy-derived precursors is discussed. Specifically, the interrelationship between the precursor chemistry and low-temperature crystallization was determined. Additionally, the ferroelectric properties of stoichiometric thin films are reported.

That is, the present inventors, in order to realize the low-temperature processes, have considered precursor chemistry suitable for low-temperature crystallization and have investigated composite metal alkoxides, and besides, have formed a thin film employing a synthesized composite alkoxide by optimizing precursor solution chemistry, and have investigated the crystallization of the thin film and ferroelectric properties thereof; as a result, they have synthesized a composite alkoxide, have clarified the molecular structure of the composite alkoxide, have controlled the structure to an atomic arrangement similar to that of the sub-lattice of a desired crystal structure, have realized low-temperature crystallization, and have clarified the fact that since the activated energy regarding crystallization of an amorphous gel before a heat treatment prepared by the hydrolysis polycondensation reaction of alkoxide molecules with an atomic arrangement similar to that of crystals is small, as a result, crystallization can be performed at a low temperature, which has led to the accomplishment of the present invention.

That is, it is an objective of the present invention to provide a process for preparing an Sr—Bi—Ta or Nb-based composite alkoxide with the structure of an atomic arrangement controlled.

It is another objective of the present invention to provide a process for preparing a precursor composite alkoxide solution for an Sr—Bi—Ta or Nb-based thin film with the structure of an atomic arrangement controlled to be similar to that of the sub-lattice of the crystal of a desired thin film.

It is still another objective of the present invention to provide a process for preparing a layer-structured perovskite thin film of bismuth-based compounds, employing the above composite alkoxide solution.

It is still another objective of the present invention to provide an Sr—Bi—Ta or Nb-based composite alkoxide with the structure of an atomic arrangement controlled, which is prepared by the above process.

It is still another objective of the present invention to provide a ferroelectric memory element, utilizing the above layer-structured perovskite thin film of bismuth-based compouds.

SUMMARY OF THE INVENTION

As described above in detail, the present invention relates to a method for producing an Sr—Bi—Ta or Nb-based composite alkoxide with the structure of an atomic arrangement controlled, having a metal atomic ratio of Sr:Bi:Ta or Nb=1:2:2, characterized in that an Sr alkoxide ($Sr(OR)_2$) prepared from an Sr metal is allowed to react with a Bi alkoxide ($Bi(OR)_3$) in alcohol to produce an Sr—Bi double alkoxide ($Sr[Bi(OR)_4]_2$), and subsequently the alkoxide is allowed to react with a Ta alkoxide ($Ta(OR)_5$) or an Nb alkoxide ($Nb(OR)_5$).

The present invention provides a novel invention exhibiting extraordinary effects that a precursor composite alkoxide with the structure of an atomic arrangement controlled is synthesized, the alkoxide solution is optimized in the molecular structure thereof to the crystalline structure of a desired thin film, the crystallization of a thin film at a low temperature of an initial temperature of crystallization below 550° C. is made possible by employing the synthesized composite alkoxide, and that the formed thin film has excellent ferroelectric properties.

DETAILED DESCRIPTION OF THE INVENTION

The present invention dissolving the above problems relates to the following (1)–(6).

(1) A method for producing an Sr—Bi—Ta or Nb-based composite alkoxide with the structure of an atomic arrangement controlled, having a metal atomic ratio of Sr:Bi:Ta or Nb=1:2:2, characterized in the processes which comprises of reacting an Sr alkoxide ($Sr(OR)_2$) prepared from an Sr metal with a Bi alkoxide ($Bi(OR)_3$) in alcohol to produce an Sr—Bi double alkoxide ($Sr[Bi(OR)_4]_2$), and subsequently reacting the obtained alkoxide with a Ta alkoxide ($Ta(OR)_5$) or an Nb alkoxide ($Nb(OR)_5$).

(2) A method for producing a precursor composite alkoxide solution for an Sr—Bi—Ta or Nb-based thin film with the structure of an atomic arrangement similar to that of the sub-lattice of the crystal structure of a desired thin film, characterized in that the above composite alkoxide is hydrolyzed by water with a molar ratio of from 1/18 to 1/6.

(3) A method for producing a layer-structured perovskite thin film of bismuth-based compounds, characterized in the processes which comprises of employing the above solution of an Sr—Bi—Ta or Nb-based composite alkoxide or the above precursor composite alkoxide solution, forming a thin film on the surface of a base such as a metal, an oxide single crystal, ceramics or glass according to a coating method such as dip coating or spin coating, or a printing method, and then subjecting the thin film to drying, calcination and a heat treatment.

(4) A method for producing the above layer-structured perovskite thin film of bismuth-based compounds, wherein a heat treatment at a low temperature below 550° C. according to a rapid temperature-rising heat treatment is performed to crystallize the film.

(5) An S—Bi—Ta or Nb-based composite alkoxide with the structure of an atomic arrangement controlled, having a metal atomic ratio of Sr:Bi:Ta or Nb=1:2:2, which is produced by the above process.

(6) A ferroelectric memory element, characterized in that the above layer-structured perovskite thin film of bismuth-based compounds is utilized.

As an Sr alkoxide ($Sr(OR)_2$) in the present invention can be mentioned, for example, $Sr(OC_2H_4OCH_3)_2$, as a Bi alkoxide ($Bi(OR)_3$), for example, $Bi(OC_2H_5)_3$, as an Sr—Bi double alkoxide ($Sr[Bi(OR)_4]_2$), for example, $Sr[Bi(OC_2H_4OCH_3)_4]_2$, as a Ta alkoxide ($Ta(OR)_5$), for example, $Ta(OC_2H_5)_5$, and as an Nb alkoxide ($Nb(OR)_5$), for example, $Nb(OC_2H_5)_5$, preferably respectively; however, they are not restricted to the above, and proper alkoxides represented by the general formula $(OR)_n$, (R: hydrocarbon radical) can be employed.

Moreover, as an alcohol of a solvent can be mentioned, for example, methoxy ethanol preferably; however, it is not restricted thereto, and proper alcohols can be employed.

As the process of the present invention can be exemplified the reaction process described in Examples to be described later; however, it is not restricted thereto, and similar processes with the same conditions enabling the structure of an atomic arrangement to be controlled can be employed similarly.

In the present invention, a precursor composite alkoxide solution is prepared by performing the hydrolysis polycondensation reaction of a prepared composite alkoxide employing water; in this case, water with a molar ratio of from 1/18 to 1/6 is employed preferably.

Next, a thin film of said composite alkoxide is formed on the surface of a base employing the above solution of an Sr—Bi—Ta or Nb-based composite alkoxide (precursor composite alkoxide solution); in this case, as a coating method can be mentioned, for example, dip coating, spin coating and a printing method preferably; however, it is not restricted to the above, and any method with the same effects can be utilized properly.

As a base can be mentioned, for example, metals, oxide single crystals, ceramics and glass; however, proper bases can be employed, irrespective of material and form.

The composite alkoxide synthesized according to the present invention is a novel material with the structure of an atomic arrangement controlled, and in particular, the molecular structure thereof has never been reported. Said composite alkoxide has the structure of an atomic arrangement controlled to be similar to that of the sub-lattice of a desired thin film, and hence, the activated energy regarding crystallization of an amorphous gel before a heat treatment prepared by the hydrolysis polycondensation reaction of said molecules is small, and as a result, crystallization can be performed at a low temperature. It has been revealed thereby that crystallizability is improved sharply at an initial temperature of crystallization below 550° C. and besides at a temperature up to 700° C.

Thus, the present invention provides a novel invention exhibiting extraordinary effects that a precursor composite alkoxide with the structure of an atomic arrangement controlled is synthesized, the alkoxide solution is optimized in the molecular structure thereof to the crystalline structure of a desired thin film, the crystallization of a thin film at a low temperature of an initial temperature of crystallization below 550° C. is made possible by employing the synthesized composite alkoxide, and that the formed thin film has excellent ferroelectric properties.

EXAMPLES

Hereunder, the present invention will be described in more detail according to Examples; however, the present invention is not restricted to the following Examples.

Example 1

Preparation of Precursor Solutions

Figure 1:
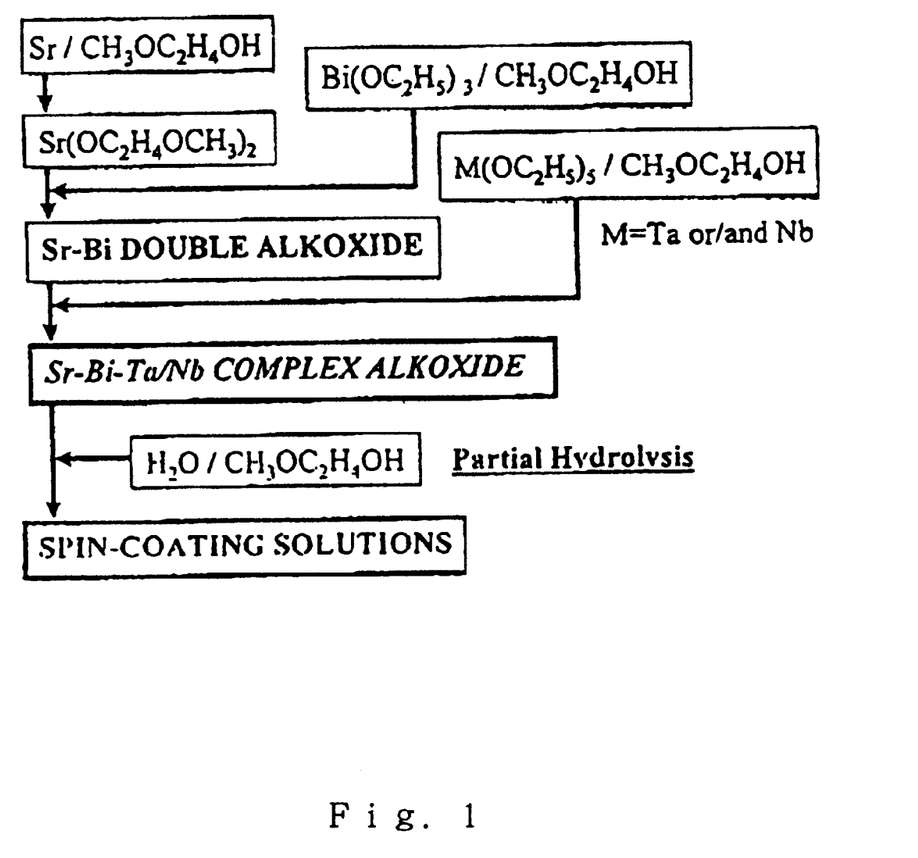
FIG. 1 shows a flow diagram for preparation of SBT and SBN precursor solutions.

FIG. 1 shows a flow diagram for preparation of precursor solutions. The following procedure was carried out in a dry inert gas ($N_2$ or He) atmosphere. Strontium metal was dissolved in methoxyethanol ($CH_3CH_2OCH_2CH_2OH$, reagent grade) by reaction at 124° C.

Bismuth triethoxide (Bi(OEt)$_3$, Hight Purity Chemicals Co.), was added to the Sr alkoxide solution in the molar ratio of 2:1, and then heated at 124° C. for 2 hrs.

Tantalum pentaethoxide (Ta(OEt)$_5$, High Purity Chemicals Co.), or niobium pentaethoxide (Nb(OEt)$_5$, High Purity Chemicals Co.), in the molar ratio of 2:1 with respect to Sr alkoxide, was added to the Sr—Bi alkoxide solution. Then the solutions were complexed at 78° C. for 1 hr. Next, deionized water, diluted in methoxyethanol in the volume ratio of 1:9, was added to Sr—Bi—M (M=Ta, Nb) alkoxide complex in the molar ratio (R) of 1:18. Note, that R values of 1:9, 1:6, and 1:3 were also used for NMR studies. The complex solutions were stirred at room temperature for 1 hr after hydrolysis. The concentration of the hydrolyzed, alkoxide complex containing Sr, Bi, and M in the molar ratio 1:2:2 was 0.05 M.

The precursor solutions were stored in sealed bottles.

Analysis of the Precursors $^1$H-, $^{13}$C-(Varian Gemini 300) and $^{93}$Nb-Nuclear Magnetic Resonance Spectroscopy (NMR, 97.88 MHz, Varian Unity Plus 400), and Fourier-Transform Infrared Spectroscopy (FT-IR, Nicolet Impact 40) measurements were performed to determine the molecular structures of the precursors and to examine the effects of hydrolysis on their structures. Just before the measurements, the precursor solutions, both prehydrolyzed and unhydrolyzed, were dried at 50–60° C. by using a rotary vacuum pump. They were then diluted with nujol for FT-IR measurements and deuterized toluene (C$_7$D$_8$)with tetramethylsilane (Si(CH$_3$)$_4$) for NMR measuremets. For $^{93}$Nb-NMR measurements, the chemical shifts were referenced to tetramethylammonium hexachloroniobate ((CH$_3$)$_4$N(NbCl$_6$))in deuterized acetonitrile (CD$_3$CN).

Results

In the $^1$H-NMR for Sr(OCH$_2$CH$_2$OCH$_3$)$_2$, signals at 3.92, 3.50 and 3.34 ppm are due to hydrogen of the methylene group that is bonded to hydroxyl group (CH$_3$OCH$_2$CH$_2$O—Sr), hydrogen of the methylene group (CH$_3$OCH$_2$CH$_2$O—Sr), and hydrogen of the terminal methyl group (CH$_3$OCH$_2$CH$_2$O—Sr), respectively. In the $^{13}$C-NMR for Sr(OCH$_2$CH$_2$OCH$_3$)$_2$, three signals at 77.1, 61.8, and 58.8 ppm are due to carbon of the methylene group (CH$_3$OCH$_2$CH$_2$O—Sr), carbon of the methylene group that is bonded to strontium (CH$_3$OCH$_2$CH$_2$O—Sr) via the adjacent oxygen, and carbon of the terminal methyl group (CH$_3$OCH$_2$CH$_2$O—Sr).

In the $^1$H-NMR for Sr[Bi(OCH$_2$CH$_2$OCH$_3$)$_4$]$_2$, signals appeared at 4.37, 3.53, and 3.33 ppm. In the $^{13}$C-NMR for Sr[Bi(OCH$_2$CH$_2$OCH$_3$)$_4$]$_2$, three signals appeared at 77.6, 62.4, and 58.5 ppm. The small differences in chemical shifts in comparison to Sr(OCH$_2$CH$_2$OCH$_3$)$_2$ are indicative of the formation of Sr—Bi double alkoxide, wherein the hydrogens and carbons are in a chemically equivalent environment. A previous report on formation and structure of Sr[Bi(OEt)$_4$]$_2$ double alkoxide is consistent with this explanation.[11]

The $^1$H-NMR for Nb(OCH$_2$CH$_2$OCH$_3$)$_5$ exhibited signals at 4.57, 3.53, and 3.29 ppm. The $^{13}$C-NMR exhibited three signals at 74.5, 72.7 and 58.7 ppm.

Additionally, the $^1$H-NMR for Sr[Nb(OCH$_2$CH$_2$OCH$_3$)$_6$]$_2$ consisted of signals at 4.48, 3.48, and 3.37 ppm, and the $^{13}$C-NMR consisted of three signals at 75.8, 69.9, and 59.0 ppm. These results are again indicative of the formation of Sr—Nb double alkoxide. Previously, a Sr[Nb(OPr)$_6$]$_2$ double alkoxide has been reported to have a structure comprising of two NbO$_6$ octahedra connected by a Sr atom.[12]

In the $^1$H-NMR for the unhydrolyzed SBN precursor, signals appeared at 4.52, 3.48, and 3.37 ppm. In the $^{13}$C-NMR, the strong three signals appeared at 75.8, 70.0, and 59.0 ppm, and the satelite signals appeared at 77.6, 62.4, and 58.4 ppm. Interestingly, the main $^1$H and $^{13}$C signals closely corresponded to the signals of Sr[Nb(OCH$_2$CH$_2$OCH$_3$)$_6$]$_2$, whereas the satelite signals closely corresponded to the signals of Sr[Bi(OCH$_2$CH$_2$OCH$_3$)$_4$]$_2$. The small differences in chemical shifts of SBN precursor from those of the original double alkoxides indicates that the SBN precursor is also a complex molecule which consists of Sr—O—Nb bonds (i.e., Sr connecting two NbO$_6$ octahedra) and Sr—O—Bi bonds. Note that this arrangement of the metals and oxygens in the SBN precursor molecule is structurally similar to that of a sub-lattice of a SBN crystal.

The chemical shifts of the hydrolyzed SBN precursors did not change when the molar ratio of water to the alkoxy groups was 1:18. This indicates that the hydrolysis-polycondensation reactions proceed homogeneously to form clear oligomeric solutions having long lifetimes. The absence of precipitation, due to rapid inhomogeneous reactions, attests to this phenomenon. In essence, the sub-lattice unit of the unhydrolyzed molecule is preserved in the cross-linked oligomeric species as condensation proceeds. This is the origin of the low crystallization temperature.

Analogous results concerning the chemical environments of hydrogen and carbon of the methoxyethoxy groups in the SBT system were observed. Like the SBN precursor molecule, note that this arrangement of the metals and oxygens in the SBT precursor molecule is structurally similar to that of a sub-lattice of a SBT crystal.

Since $^{93}$Nb is appropriate nuclear for NMR, the chemical shifts for unhydrolyzed and hydrolyzed SBN precursors were measured to further probe the chemical environment of Nb in the octahedral unit. Two signals appeared at −1240 ppm and −1160 ppm in the $^{93}$Nb-NMR for Nb(OEt)$_5$. This means that the commercial chemical was a mixture of monomer and dimer. The latter is reported to have a structure in which two oxygen-octahedra share an edge. [13]

In the $^{93}$Nb-NMR of Nb(OCH$_2$CH$_2$OCH$_3$)$_5$, a broad signal, indicative of an asymmetric penta-fold environment of the Nb atom in a monomeric unit, appeared at −1170 ppm.

The broadening behavior of $^{93}$Nb signal for Nb alkoxides, with ligand substitution, is also identified in a previous report. [14] In contrast, the $^{93}$Nb-NMR for the unhydrolyzed SBN precursor exhibits a sharp signal at −1140 ppm with a half-width value of 14,000 Hz.

This can be explained by Nb atoms in a chemically equivalent environment but in a symmetric, octahedron site in the molecule. Note also that the $^{93}$Nb-NMR signal of the SBN precursor after partial hydrolysis was identical to the unhydrolyzed precursor. Additionally, in the $^{93}$Nb-NMR for Sr[Nb(OCH$_2$CH$_2$OCH$_3$)$_6$]$_2$, which was prepared for a reference, a signal at −1150 ppm with a half-width value of 11,400 Hz was observed. This difference in the chemical shifts and the half-width values for the SBN precursor and Sr[Nb(OCH$_2$CH$_2$OCH$_3$)$_6$]$_2$ can be attributed to the presence of Bi—O bonds in the former. Specifically, the broad signal in the SBN precursor stems from the lowering of symmetry of the octahedral Nb site due to Bi—O bonds. This result clearly provides further evidence of the insertion of Bi—O bonds to an unit consisting of two NbO$_6$ octahedra connected by a Sr atom.

Again, the structural similarity with respect to the layer-structured perovskite sub-lattice is confirmed. In the FT-IR spectrum of Sr[Bi(OCH$_2$CH$_2$OCH$_3$)$_4$]$_2$, peaks due to C—O vibrations appeared at 982, 962, 895 and 837 cm$^{-1}$, and peaks due to Bi—O vibrations and Sr—O vibrations appeared at 591, 555, 525, and 461 cm$^{-1}$.

The peak shifts in the latter (M—O vibrations), with respect to individual Sr alkoxide and Bi alkoxide, are due to the formation of Sr[Bi(OCH$_2$CH$_2$OCH$_3$)$_4$]$_2$ double alkoxide. A similar shift has been reported for the formation of Sr[Bi(OEt)$_4$]$_2$ double alkoxide.[11] In the FT-IR spectrum of Nb(OCH$_2$CH$_2$OCH$_3$)$_5$, peaks due to C—O vibrations appeared at 981, 963, 922, 894, 837 and 790, and peaks due to M—O vibrations appeared at 592 and 496 cm$^{-1}$.

In the spectrum of the SBN precursor, peaks appeared at 981, 965, 915, 895, 837, 583, and 486 cm$^{-1}$.

Comparison of the spectrum of the SBN precursor to the spectra of Sr[Bi(OCH$_2$CH$_2$OCH$_3$)$_4$]$_2$ and Nb(OCH$_2$CH$_2$OCH$_3$)$_5$ indicated that the peaks around at 583 and 486 cm$^{-1}$ are due to vibration modes stemming from M—O bonds in the complex molecule.

To identify these peaks, a comparison was made with the reference Sr[Nb(OCH$_2$CH$_2$OCH$_3$)$_6$]$_2$, which exhibited absorption peaks, due to Nb—O vibrations, at 590 and 483 cm$^{-1}$. Therefore, as concluded in the NMR studies, the SBN precursor molecule contained NbO$_6$ octahedra like Sr[Nb(OCH$_2$CH$_2$OCH$_3$)$_6$]$_2$. Analogous results concerning the chemical bonds in the SBT system were obtained. Therefore, the SBT precursor molecule contained two TaO$_6$ octahedra like Sr[Ta(OCH$_2$CH$_2$OCH$_3$)$_6$]$_2$.

Results of $^1$H-, $^{13}$C-NMR, and FT-IR indicate that SBT and SBN precursors contain Sr—O—M (M; Ta or Nb) bonds comprising of two MO$_6$ octahedra connected by a Sr atom, and Sr—O—Bi links. These precursors are structurally identical.

Additionally, $^{93}$Nb-NMR confirms a symmetric Nb site within the NbO$_6$ octahedra, which are connected by a Sr atom and bonded to two Bi atoms.

Figure 2:
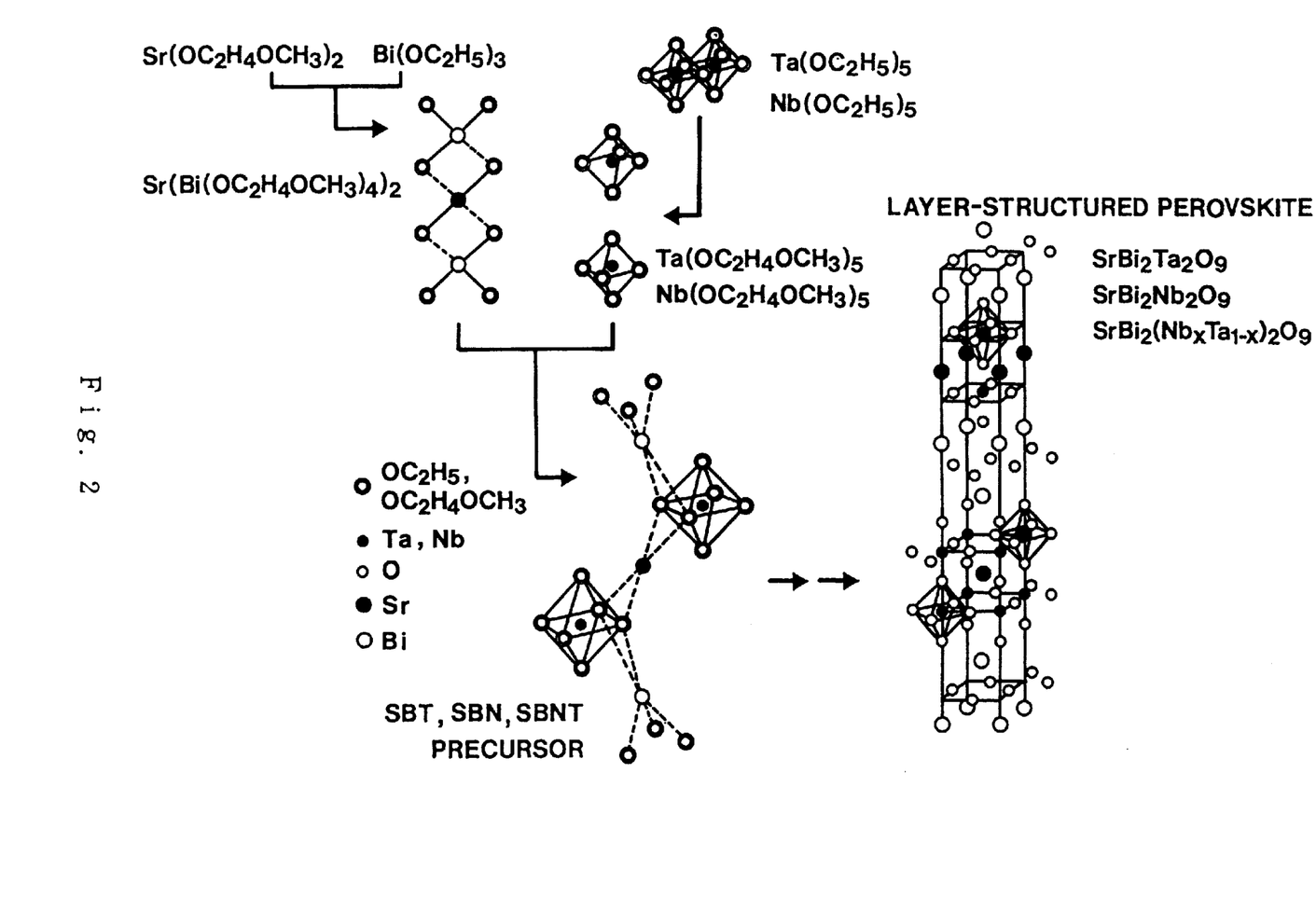
FIG. 2 shows proposed precursor chemistry for the layer-structured perovskite thin films.

FIG. 2 shows the proposed precursor chemistry for the layer-structured perovskite compounds. These features of SBT and SBN precursors are identical to the sub-lattices of SBT and SBN crystals.

Additionally, the sub-lattice units are preserved in the cross-linked oligomeric species as condensation proceeds. As discussed elsewhere,[15], [16] this is the origin of the low crystallization temperature.

Conclusion

The precursor molecules for the layer-structured perovskite thin films of SBT and SBN were prepared by the reactions of Sr[Bi(OCH$_2$CH$_2$OCH$_3$)$_4$]$_2$ and M(OCH$_2$CH$_2$OCH$_3$)$_5$ (M; Ta or Nb).

These molecules consisted of Sr—O—M bonds (i.e., a Sr atom connecting two MO$_6$ octahedra) and Sr—O—Bi bonds of which the Bi atom bonding to the MO$_6$ octahedron. The arrangement of the metals and oxygens in these molecules was identical to the sub-lattice of the layer-structured perovskite crystal. The addition of a trace amount of water to these molecules in the molar ratio of 1:18 produced homogeneously condensed spin-coating solutions. The sub-lattice units are preserved in the cross-linked oligomeric species as condensation proceeds. The gel films deposited from these precursor soltuions could crystallize at temperatures below 550° C.

Example 2

Preparation and Crystallization of Thin Films

Thin films were prepared on Si(100) or Pt-passivated silicon (Pt3000 Å /Ti50 Å /SiO$_2$/Si(100)) substrates by spin-coating aged, hydrolyzed precursor solutions. The precursor solutions were prepared by reactions of Sr—Bi double methoxyethoxide and Ta/Nb ethoxide in methoxyethanol followed by the partial hydrolysis. Details for the preparation of precursor solutions were described elsewhere.[9], [10] Each layer was deposited at 2000 rpm for 80 s, dried at 150° C. and calcined at 350° C. in air. The layer was subjected to various heat treatments in oxygen. By the use of a rapid thermal annealing unit, the thin-film gels were elevated at a rate of 200° C./s to the desired crystallization temperatures and heat treated for 10 minutes. Additionally, some thin films were heated in a conventional furnance at a heating rate of 2° C./min. The thicknesses of the films were increased by repetition of the aforementioned treatments.

Characterization of Thin Films

X-ray diffraction measurements (XRD, Rigaku D/Max-II B Diffractometer), with CuKα radiation, were performed to determine the crystal phase and the crystallographic orientation of the thin films. The acceleration voltage and current were 50 kV and 30 mA, respectively. The compositions of the films were determined by Rutherford Backscattering Spectroscopy (RBS, Tandetron, General Ionex) and simulation. Film thicknesses were determined by using an ellipsometer (VASE, M-44, J. A. Woollam Co.). Prior to the electrical measurements, top Pt electrodes were deposited by electron beam evaporation, which was followed by annealing at the crystallization temperatures. The ferroelectric hysteresis properties were measured by using a Sawyer-Tower circuit and a digital signal analyzer (DSA602, AFG2020, Tektronix Inc)

Result

Low-Temperature Crystallization of SBT and SBN Thin Films

By RBS analysis, the atomic ratios of metals in the SBT and SBN thin films after heat treatments were determined to be identical to those of the precursors.

Figure 3:
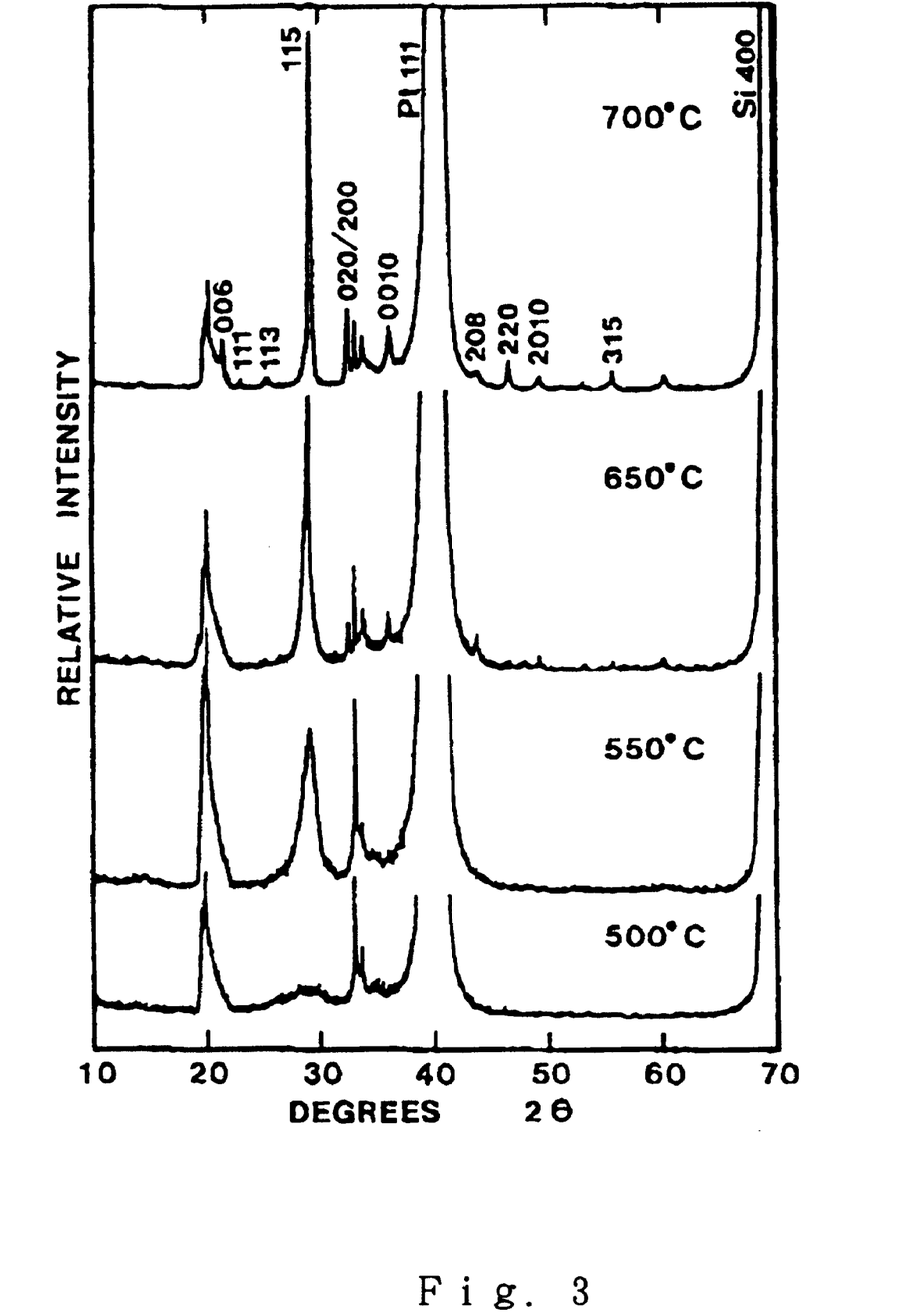
FIG. 3 shows XRD patterns of SBT thin films after rapid thermal annealing at various temperatures.

FIG. 3 shows XRD profiles of SBT thin films on Pt-passivated silicon substrates after rapid thermal annealing at various temperatures. The perovskite thin films were found to be single-phase. Although the thin films crystallized below 550° C., crystalline perfection improved and crystallite size increased upon heat treatment up to 700° C. The low crystallization temperature can be explained as follows. As described elsewhere,[9], [10] since the molecular structure of the SBT and SBN precursors is preserved upon hydrolysis, the homogeneous gels that form after spin-coating have amorphous structures. Due to the structural similarity of the precursors to that of the crystalline sub-lattice, the activation energies for the amorphous gel to the crystalline phase transformation are expected to be low. This would be a direct result of an interfacecontrolled, thermally mediated bond rearrangement process. A similar process, with low activation energies, has been reported for the crystallization of homogeneous PbTiO$_3$ gels derived by the alkoxide route.[11] Also, by alkoxy-derived precursor control, low crystallization temperatures in the Ba(Mgt$_{1/3}$Ta$_{2/3}$)O$_3$ ceramics have been reported.[12]

The SBT thin films exhibited preferred orientation in the (115) plane and this is preferable to c-axis orientated films with respect to ferroelectric properties. Note also that neither the fluorite nor pyrochlore phases were observed by use of the present technique. These attributes of low-temperature crystallization and preferred orientation are considered significant improvements over previous reports on liquid deposition technique.[2]–[8]

Figure 4:
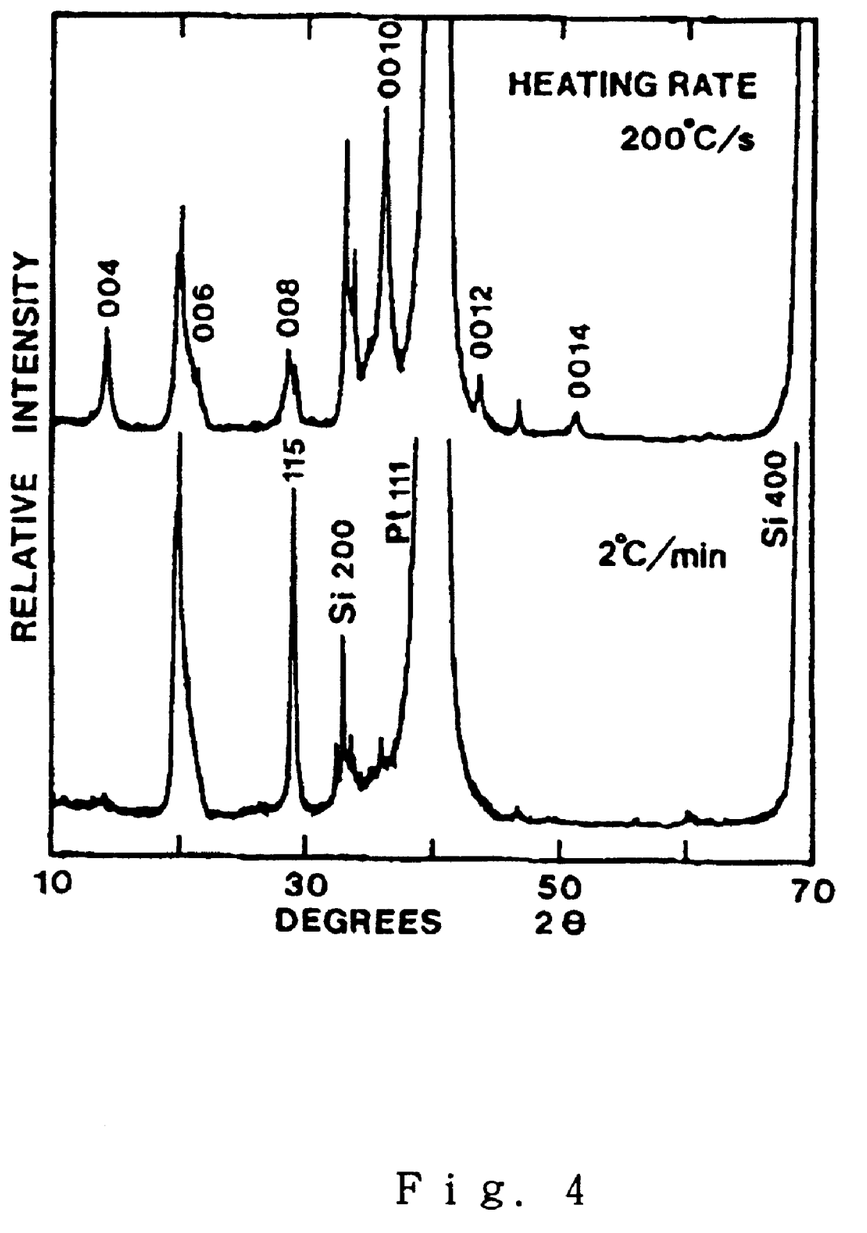
FIG. 4 shows XRD patterns of SBN thin films after heat treatment at 700° C. with various heating rates.

FIG. 4 shows XRD patterns of SBN thin films on Pt-passivated silicon substrates after heat treatments at 700°

C., with two different heating rates. Although the thin films were converted to single-phase perovskite, they exhibited different degrees of orientation. The thin film subjected to a heating rate of 200° C./s (by rapid thermal annealing) and heat treated for 10 minutes were c-axis oriented. In contrast, the thin films subjected to a heating rate of 2° C./min and heat treated for 10 minutes showed highly preferred (115) orientation. This heating-rate dependence of the orientation has not been reported. Apparently, the low heating rate promotes the nucleation and growth of the densely packed (115) plane. Although, the crystal structure of SBN and SBT are identical, and the lattice parameters are reported to be: a=b=5.512 Å, and c=25.00 Å for SBT, and a=b=5.506 Å, and c=25.05 Å for SBN, [13)-14)] the orientation of SBT thin films was independent of the heating rate. The heating ratedependence of the crystallographic orientation between the SBT and SBN thin films may stem from the higher refractoriness of SBN over SBT.

Ferroelectric Properties of SBT and SBN Thin Films

Figure 5:
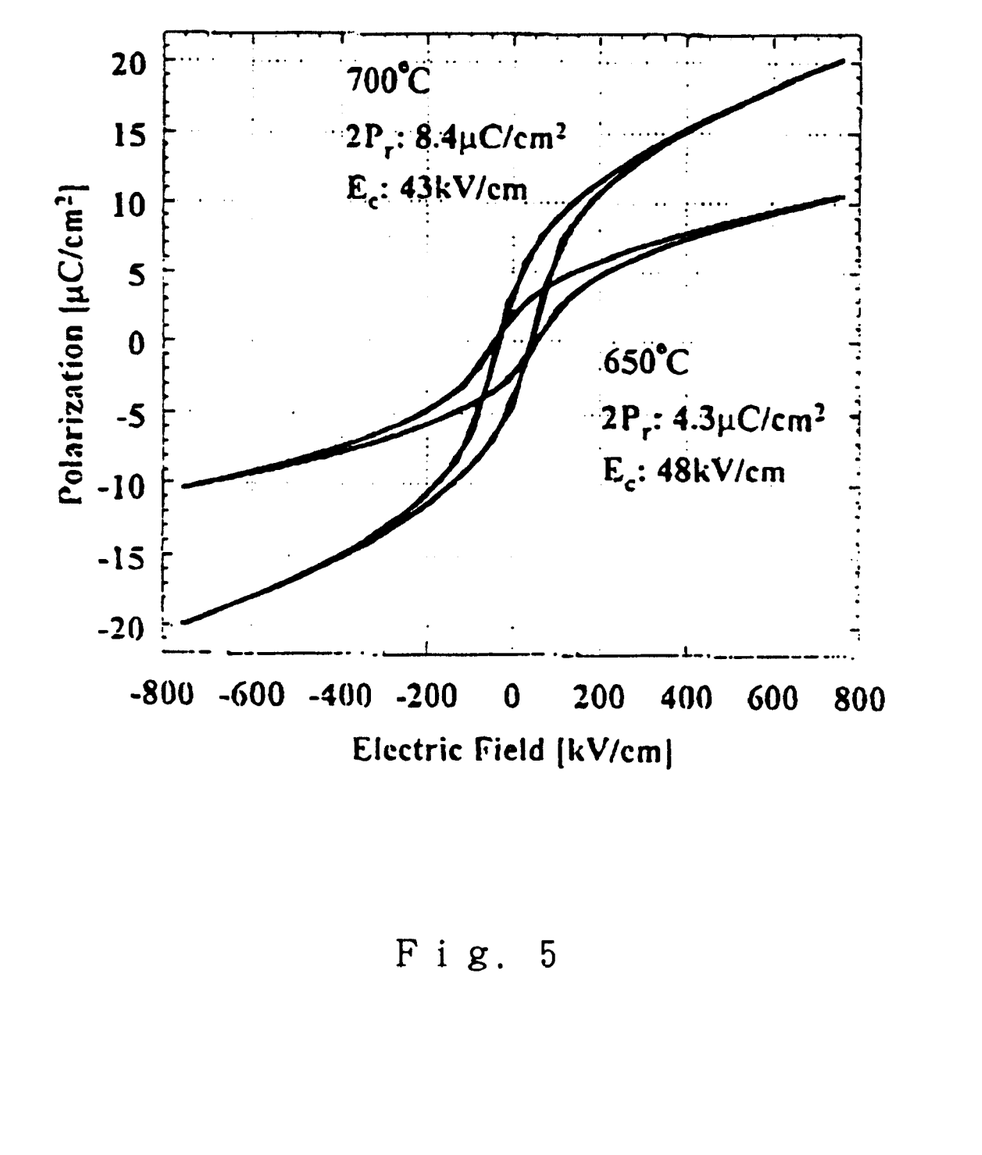
FIG. 5 shows the hysteresis loops at an applied voltage of 5 V for 130 nm SBT thin films after rapid thermal annealing.

FIG. 5 shows the hysteresis loops for SBT thin films heat treated at 650° C. and 700° C. with a heating rate of 200° C./s. The remnant polarization ($2P_r$) and the coercive field ($E_c$) at an applied voltage of 5 V were 4.3 $\mu C/cm^2$ and 56 kV/cm, 8.4 $\mu C/cm^2$ and 43 kV/cm, respectively, for the 650° C. and 700° C. heat treated films. Note, that in addition to the $2P_r$ being higher and the $E_c$ being lower for 700° C. heat treated film, the film saturated at about 3.0V. This behavior may be due to a higher crystalline perfection, relatively larger crystallite size, and denser nature of the thin film heated at 700° C.

Figure 6:
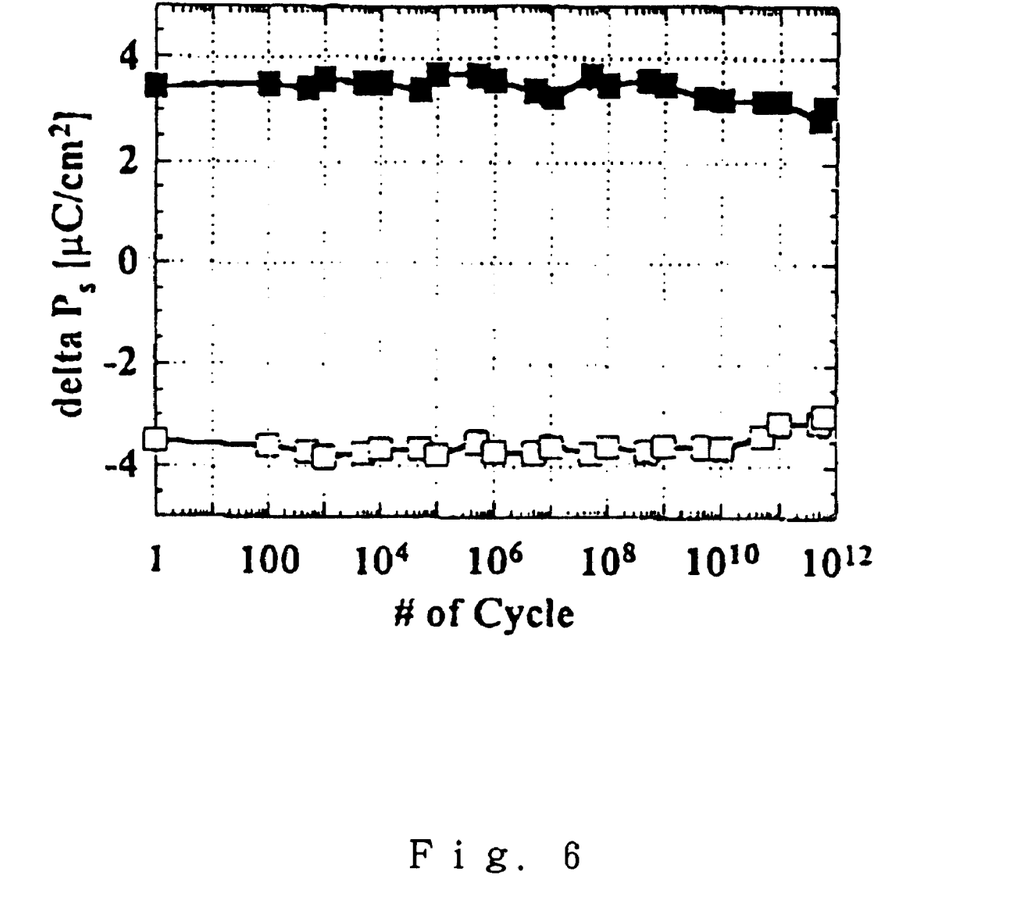
FIG. 6 shows fatigue behavior of Pt/SBT/Pt capacitors at an applied voltage of 3 V and frequency 1 MHz.

Additionally, the fatigue behavior for the 700° C. heat treated SBT film is shown in FIG. 6. Upon $10^{10}$ cycles of switching at an applied voltage of 3 V, the thin film did not exhibit any change in the polarization.

Conclusions

The gel thin films were deposited on Pt-passivated silicon substrates by spin-coating the alkoxy-derived precursor solutions. The films crystallized to single-phase perovskite SBT after rapid thermal annealing in an oxygen atmosphere at temperatures below 550° C.

The crystalline perfection improved and the crystallite size increased with temperatures up to 700° C. The low crystallization temperature can be explained by the low activation energy for the amorphous gel to the crystalline phase transformation.

The SBT thin films heated at 700° C. exhibited a preferred (115) orientation independently of the heating rate, however, the SBN thin films exhibited heating rate-dependence of the crystallographic orientation. The SBN thin films subjected to a heating rate of 2° C./s and heat treated for 10 minutes at 700° C. showed highly preferred (115) orientation. The heating rate-dependence of the crystallographic orientation between the SBT and SBN thin films may stem from the higher refractoriness of SBN and SBT.

SBT thin films strongly exhibiting (115) preferred orientation had improved ferroelectric properties. The remnant polarization ($2P_r$) and the coercive electric field ($E_c$) at an applied voltage of 5 V were 8.4 $\mu C/cm^2$ and 43 kV/cm, respectively.

REFERENCES (NO.1)

[1] C. A. Paz de Araujo, J. D. Cuchiaro, L. D. McMillan, M. C. Scott and J. F. Scott, Nature, 374, 627 (1995)
[2] J. Robertson, C. W. Chen, W. L. Warren and C. D. Gutleben, Appl. Phys. Lett., 69 [12] 1704 (1996).
[3] T. Atsuki, N. Soyama, T. Yonezawa and K. Ogi, Jpn. J. Appl. Phys., 34 [9B] 5096 (1995).
[4] Y. Ito, M. Ushikubo, S. Yokoyama, H. Matsunaga, T. Atsuki, T. Yonezawa and K. Ogi, Jpn. J. Appl. Phys., 35 [9B] 4925 (1996).
[5] T. Hayashi, H. Takahashi and T. Hara, Jpn. J. Appl. Phys., 35 [9B] 4952 (1996).
[6] T. J. Boyle, C. D. Buchheit, M. A. Rodriguez, H. N. Al-Shareef, B. A. Hernandez, B. Scott and J. W. Ziller, J. Mater, Res., 11 [9] 2274 (1996).
[7] M. A. Rodriguez, T. J. Boyle, B. A. Hernandez, C. D. Buchheit, and M. 0. Eatough, J. Mater, Res., 11 [9] 2282 (1996).
[8] I. Koiwa, T. Kanehara, J. Mita, T. Iwabuchi, T. Osaka, A. Ono and M. Maeda, Jpn. J. Appl. Phys., 35 [9B] 4946 (1996).
[9] K. W. Bagnall and D. Brown, J. Chem. Soc., [9] 3021 (1964).
[10] R. G. Kidd and H. G. Spinney, Inorg, Chem., 12 [9] 1967 (1973).
[11] S. Katayama and M. Sekine, J. Mater. Res., 6 [1] 36 (1991).
[12] S. Govil, P. N. Kapoor, R. C. Mehrotra, J. Inorg. Nucl. Chem., 38, 172 (1976).
[13] D. C Bradley and R. C. Holloway, J. Chem. Soc. A, 219 (1968).
[14] W. Sakamoto, T. Yogo, K. Kikuta, K. Ogiso, A. Kawase and S. Hirano, J. Am. Ceram. Soc. 79 [9] 2283 (1996).
[15] K. Kato, C. Zheng, J. M. Finder, S. K. Dey, and Y. Torii, submitted to J. Am. Ceram. Soc.
[16] K. Kato, J. M. Finder, S. K. Dey, and Y. Torii, Proceedings of ISIF97, in printing.

REFERENCES (NO.2)

1) C. A. Paz deAraujo, J. D. Cuchiaro, L. D. Mcmillan, M. C. Scott and J. F. Scott, Nature, 374, 627 (1995)
2) T. Atsuki, N. Soyama, T. Yonezawa and K. Ogi, Jpn. J. Appl. Phys., 34 [9B] 5096 (1995).
3) T. Noguchi, T. Hase and Y. Miyasaka, Jpn. J. Appl. Phys., 35 [9B] 4900 (1996).
4) Y. Ito, M. Ushikubo, S. Yokoyama, H. Matsunaga, T. Atsuki, T. Yonezawa and K. Ogi, Jpn. J. Appl. Phys., 35 [9B] 4925 (1996).
5) T. Hayashi, H. Takahashi and T. Hara, Jpn. J. Appl. Phys., 35 [9B] 4952 (1996).
6) T. J. Boyle, C. D. Buchheit, M. A. Rodriguez, H. N. Al-Shareef, B. A. Hernandez, B. Scott and J. W. Ziller, J. Mater, Res., 11 [9] 2274 (1996).
7) M. A. Rodriguez, T. J. Boyle, B. A. Hernandez, C. D. Buchheit, and M. 0. Eatough, J. Mater, Res., 11 [9] 2282 (1996).
8) I. Koiwa, T. Kanehara, J. Mita, T. Iwabuchi, T. Osaka, A. Ono and M. Maeda, Jpn. J. Appl. Phys., 35 [9B] 4946 (1996).
9) K. Kato, C. Zheng, J. M. Finder, S. K. Dey, and Y. Torii, submitted to J. Am. Ceram. Soc.
10) K. Kato, C. Zheng, S. K. Dey, and Y. Torii, Proceedings of ISIF97, in printing.
11) P. R. Coffman, C. K. Barlingay, A. Gupta and S. K. Dey, J. Sol-Gel Sci. Tech., 6, 83 (1996).
12) S. Katayama, I. Yoshinaga, N. Yamada and T. Nagai, J. Am. Ceram. Soc. 79 [8] 2059 (1996).
13) G. A. Smolenskii, V. A. Isupov and A. L. Agranovskaya, Sov. Phys. Solid State., 1, 149 (1959).
14) G. A. Smolenskii, V. A. Isupov and A. L. Agranovskaya, Sov. Phys. Solid State., 3 [3] 651 (1961).

As described above in detail, the present invention relates to a method for producing an Sr—Bi—Ta or Nb-based composite alkoxide with the structure of an atomic arrangement controlled, having a metal atomic ratio of Sr:Bi:Ta or Nb=1:2:2, characterized in that an Sr alkoxide ($Sr(OR)_2$) prepared from an Sr metal is allowed to react with a Bi alkoxide ($Bi(OR)_3$) in alcohol to produce an Sr—Bi double alkoxide ($Sr[Bi(OR)_4]_2$), and subsequently the alkoxide is allowed to react with a Ta alkoxide ($Ta(OR)_5$) or an Nb alkoxide ($Nb(OR)_5$); according to the present invention, extraordinary effects are exhibited that a novel Sr—Bi—Ta or Nb-based composite alkoxide with the structure of an atomic arrangement controlled can be synthesized, a precursor composite alkoxide solution of an amorphous gel with the structure of an atomic arrangement controlled to be similar to that of the sub-lattice of the crystal structure of a desired thin film can be obtained, a thin film can be formed on the surface of a base at an initial temperature of crystallization below 550° C. by employing said precursor composite alkoxide solution, and that thereby, a layer-structured perovskite thin film of bismuth-based compounds with excellent ferroelectric properties can be synthesized at a low-temperature process.

What is claimed is:

1. A method for producing an Sr—Bi—Ta or Nb-based composite alkoxide with the structure of an atomic arrangement controlled, having a metal atomic ratio of Sr:Bi:Ta or Nb=1:2:2, characterized in the processes which comprises of reacting an Sr alkoxide ($Sr(OR)_2$) prepared from an Sr metal with a Bi alkoxide ($Bi(OR)_3$) in alcohol to produce an Sr—Bi double alkoxide ($Sr[Bi(OR)_4]_2$), and subsequently reacting the obtained alkoxide with a Ta alkoxide ($Ta(OR)_5$) or an Nb alkoxide ($Nb(OR)_5$).

2. A method for producing a precursor composite alkoxide solution for an Sr—Bi—Ta or Nb-based thin film with the structure of an atomic arrangement controlled to be similar to that of the sub-lattice of the crystal structure of a desired thin film, wherein the composite alkoxide as claimed in claim 1 is hydrolyzed by water with a molar ratio of from 1/18 to 1/6.

3. An Sr—Bi—Ta or Nb-based composite alkoxide with the structure of an atomic arrangement controlled, having a metal atomic ratio of Sr:Bi:Ta or Nb=1:2:2, which is produced by the process as claimed in claim 1.

* * * * *